US006124524A

United States Patent [19]
James, Jr. et al.

[11] Patent Number: 6,124,524
[45] Date of Patent: Sep. 26, 2000

[54] FAE1 GENES AND THEIR USES

[75] Inventors: Douglas W. James, Jr., Berkeley; Eda Lim, Atherton; Janis Keller, Castro Valley; Hugo K. Dooner, Walnut Creek, all of Calif.

[73] Assignee: Cargill Incorporated, Wayzata, Minn.

[21] Appl. No.: 08/888,998

[22] Filed: Jul. 7, 1997

Related U.S. Application Data

[63] Continuation of application No. 08/329,603, Oct. 26, 1994, abandoned.

[51] Int. Cl.[7] ............................. A01H 5/00; C12N 15/82; C12N 5/04
[52] U.S. Cl. ........................ 800/281; 800/298; 435/468; 536/23.6
[58] Field of Search .................................. 800/205, 281, 800/286, 287, 298; 435/172.3, 320.1, 69.1, 419, 468; 536/23.6, 24.3, 24.5

[56] References Cited

U.S. PATENT DOCUMENTS

| | | | |
|---|---|---|---|
| 5,298,421 | 3/1994 | Davies | 435/320.1 |
| 5,445,947 | 8/1995 | Metz et al. | 435/69.1 |

FOREIGN PATENT DOCUMENTS

| | | | |
|---|---|---|---|
| WO 91/18985 | 12/1991 | WIPO . | |
| WO 92/03564 | 3/1992 | WIPO . | |
| 9310241 | 5/1993 | WIPO . | |
| WO 93/10240 | 5/1993 | WIPO . | |
| WO 95/15387 | 6/1995 | WIPO | C12N 15/54 |

OTHER PUBLICATIONS

Nishida, Ikuo, et al. (1993) "The gene and the RNA for the precursor to the plastid–located glycerol–3–phosphate acyl-transferase of *Arabidopsis thaliana*", *Plant Molecular Biology*, 21:267–277.

Knutzon, Deborah S., et al. (1992) "Modification of Brassica seed oil by antisense expression of a stearoyl–acyl carrier protein desaturase gene", *Proc. Natl. Acad. Sci. USA*, 89:2624–2628.

Webber, Sabine, et al. (1991) "Purification and cDNA sequencing of an oleate–selective acyl–ACP:sn–glycerol–3–phosphate acyltransferase from pea chloroplasts", *Plant Molecular Biology*, 17:1067–1076.

Kater, Martin M., et al. (1991) "cDNA cloning expression of *Brassica napus* enoyl–acyl carrier protein reductase in *Escherichia coli*", *Plant Molecular Biology*, 17:895–909.

Jaworski, Jan G., et al. (1989) "A Cerulenin Insensitive Short Chain 3–Ketoacyl–Acyl Carrier Protein Synthase in *Spinacia oleracea* Leaves", *Plant Physiol.* 90:41–44.

Schmid, Katherine M., et al. (1990) "A root acyl carrier protein–II from spinach is also expressed in leaves and seeds", *Plant Molecular Biology* 15:765–778.

Klein, Barbara, et al. (1992) "Isolation and characterization of cDNA from *Cuphea lanceolata* encoding a β–ketoacy-l–ACP reductase", *Mol Gen Genet*, 233:122–128.

Kramer, John K.G., et al. (1983) "Pathways of Fatty Acid Biosynthesis in Higher Plants with Particular Reference to Developing Rapeseed", in: *High and Low Erucic Acid Rapeseed Oils*, Academic Press Canada, Chapter 5:131–141.

Taylor, David C., et al. (1992) "Biosynthesis of Acyl Lipids Containing Very–Long Chain Fatty Acids in Microspore–Derived and Zygotic Embryos of *Brassica napus* L. cv Reston", *Plant Physiol.* 99:1609–1618.

Creach, Anne, et al. (1993) "Solubilization of Acyl–CoA Elongases from Developing Rapeseed (*Brassica napus* L.)", *JACOS* 70(11):1129–1133.

Bessoule, Jean–Jacques, et al. (1989) "Partial Purification of the Acyl–CoA Elongase of *Allium porrum* Leaves", *Archives of Biochemistry and Biophysics*, 268(2):475–484.

Fehling, Eberhard, et al. (1992) "Solubilization and partial purification of constituents of acyl–CoA elongase from *Lunaria annua*", *Biochimica et Biophysica Acta*, 1126:88–94.

James, D.W., et al. (1990) "Isolation of EMS–induced mutants in Arabidopsis altered in seed fatty acid composition", *Thero Appl Genet*, 80:241–245.

Lemieux, B., et al. (1990) "Mutants of Arabidopsis with alterations in seed lipid fatty acid composition", *Theor Appl Genet*, 80:234–240.

James, D.W., et al. (1991) "Novel seed lipid phenotypes in combinations of mutants altered in fatty acid biosynthesis in Arabidopsis", *Theor Appl Genet*, 82:409–412.

Kunst, Lkerka, et al. (1992) "Fatty acid elongation in developing seeds of *Arabidopsis thaliana*", *Plant Physiol. Biochem.*, 30(4):425–434.

Tai, Heeyoung, et al. (1993) "3–Ketoacyl–Acyl Carrier Protein Synthase III from Spinach (*Spinacia oleracea*) is Not Similar to Other Condensing Enzymes of Fatty Acid Synthase", *Plant Physiol.*, 103:1361–1367.

Arondel, Vincent, et al. (1992) "Map–Based Cloning of a Gene Controlling Omega–3 Fatty Acid Desaturation in Arabidopsis", *Science*, 258:1353–1354.

Yadav, Narendra S., et al. (1993) "Cloning of Higher Plant A ω–3 Fatty Acid Desaturases", *Plant Physiol.*, 103:467–476.

Okuley, John, et al. (1994) "Arabidopsis FAD2 Gene Encodes the Enzyme That Is Essential for Polyunsaturated Lipid Synthesis", *The Plant Cell*, 6:147–158.

James et al 1995 The Plant Cell 7:309–319.

Newman et al 1994 Plant Physiol 106:1241–1255.

Kunst et al 1992 In Seed Oils for the Future, MacKenzie et al eds., AOCS Press, pp 70–76.

Kridl et al 1993 In Control of Plant Gene Expression, Verma et al eds., CRC Press, pp 481–498.

(List continued on next page.)

*Primary Examiner*—Elizabeth F. McElwain
*Attorney, Agent, or Firm*—Fish & Richardson, P.C.

[57] ABSTRACT

The present invention provides polynucleotide sequences from FAE1 genes. FAE1 genes encode elongation enzymes which catalyze the conversion of C18 FAs to C20–C22 FAs. The polynucleotides of the invention are used to modify FAE1 gene expression and thereby modulate FA content in plant organs or parts, particularly seeds.

24 Claims, 3 Drawing Sheets

OTHER PUBLICATIONS

Desprez et al, Jun. 6, 1994, GenBank Locus ATTS 3218, Accession Z34184.

Quigley et al, Sep. 8, 1993, GenBank Locus ATTS 1282, Accession Z26005.

Desprez et al, Jun. 25, 1994, GenBank Locus ATTS 3360, Accession Z34600.

Lardizabal et al, Sep. 20, 1993, EMBL Q42839, Accession Q42839.

Murphy et al 1994 Industrial Crops & Products 3:17–27.

Vander Krol et al 1990 Plant Molecular Biology 14:457–466.

Fimmegan et al 1994 Bio/Technology 12:883–888.

Mol et al 1991 Trends in Biotechnology 9:182–183.

NUCLEOTIDE SEQUENCE OF FAE1 AROUND THE SITE OF INSERTION OF Ac

WILD-TYPE Fae1          GTTGACTACTCGTGTT fae1-ml::Ac             GTTGACTACTCGTACTACTCGTGTT Fae1' REVERTANTS (3)    GTTGACTACTCGTGTT fae1 SEGREGANT #5       GTTGACTACTCGT TCTACTCGTGTT

```
SYMBOL COMPARISON TABLE: GENCOREDISK: [Gcgcore.Data.Rundata]Swgappep.Cmp
CompCheck: 1254

GAP WEIGHT:      3.000                AVERAGE MATCH:     0.540
LENGTH WEIGHT:   0.100                AVERAGE MISMATCH: -0.396

QUALITY:    169.7                     LENGTH:  128
RATIO:      1.336                     GAPS:    1
PERCENT SIMILARITY: 94.488            PERCENT IDENTITY: 85.827

GAP LIMIT ONE: 505                    GAP LIMIT TWO: 126

1 RTHTGADDKSFRCVQQGDDENGKIGVSLSKDITDVAGRTVKKNIATLGPL  50
    |||||||||||||||:||||:|||||||:||||||:|:.|||||||||||
300 RTHTGADDKSFRCVQQEDDESGKIGVCLSKDITNVAGTTLTKNIATLGPL 349

51 ILPLSEKLLFFVTFMGKKLFKDKIKHYYVPDFKLAIDHFCIH.RSRAVID  99
    |||||||:|||.||:.|||:|||||||||||||||||||||| :|||||
350 ILPLSEKFLFFATFVAKKLLKDKIKHYYVPDFKLAVDHFCIHAGGRAVID 399

100 VLEKNLALAPIDVEASRSTLHRFGNTSS 127
    :||||| :.|||||||||||||||||||
400 ELEKNLGLSPIDVEASRSTLHRFGNTSS 427
```

FIG. 4.

FAE1 GENES AND THEIR USES

This is a Continuation of application Ser. No. 08/329,603, filed Oct. 26, 1994 now abandoned, the disclosure of which is incorporated by reference.

BACKGROUND OF THE INVENTION

The present invention relates to plant molecular biology. In particular, it provides compositions and methods useful for modulating fatty acid synthesis in plants.

Fatty acids (FAs) are the major constituents of acyl lipids in plant tissues. Acyl lipids are mainly present as triacylglycerols in the oil bodies of tissues which serve as food storage, such as seeds and the fleshy parts of fruits. These tissues are important commercial sources of fats and oils. Fatty acids are also found as glycolipids and phospholipids in other tissues, such as leaves, roots, or shoots, where they are integral components of the various cell membranes.

The principal FAs are saturated or unsaturated monocarboxylic acids with an unbranched even-numbered carbon chain. The main saturated FAs are lauric (12:0, i.e., C12 chain with no double bonds), myristic (14:0), palmitic (16:0), and stearic (18:0). The main unsaturated FAs are oleic (18:1), linoleic (18:2) and linolenic (18:3). Seed storage lipids accumulate mostly 16- and 18-carbon FAs. Oilseeds of the Cruciferae and a few other plants also accumulate C20 and C22 FAs, collectively referred to as very long chain fatty acids (VLCFAs) because of their relatively longer chain length compared to the more common FAs found in plants (see, in general, Stumpf, in *Biochemistry of Plants*, Vol. 9, Stumpf ed., Academic Press, New York, 1987) and Browse and Somerville, *Ann. Rev. Plant Physiol. Plant Mol. Biol.* 42:467–506 (1991).

The presence of VLCFAs in vegetable oils markedly affects their use. For example, erucic acid (22: 1) has detrimental nutritional effects and, thus, is undesirable in edible oils. Rapeseed oil is naturally high in erucic acid, but through a concerted breeding effort, canola lines that are almost devoid of erucic acid have been developed (Loof and Appleqvist, in *Rapeseed*, Appleqvist and Ohlson, eds. Elsevier Publishing, 1972). On the other hand, vegetable oils high in erucic acid have found many industrial uses, including use as diesel fuel and as a raw material for an array of products, including paints, corrosion inhibitors, cosmetics, plastics, pharmaceuticals, and lubricants (Murphy, *Tibtech* 10:84–87 (1992).

The biosynthesis of saturated FAs having a carbon chain up to C18 proceeds in the chloroplast via the sequential condensation of C2 units from acyl thioesters. FA synthesis is initiated by the condensation of acetyl CoA and malonyl ACP, catalyzed by the recently discovered enzyme β-ketoacyl synthase III (KASIII) (Jaworski et al., *Plant Physiol.* 90:41–44 (1989)). The enzyme ketoacyl synthase I is required for the elongation of saturated acyl-ACP from C4 to C16. The last elongation step in the chloroplast, from C16 to C18, is catalyzed by ketoacyl synthase II. Each condensation is followed by three enzymatic steps, which involve reduction and dehydration of the β-ketoacyl derivative formed by the synthase and reduction of the double bond in the corresponding enoyl-ACP intermediate (Stumpf, 1987, supra).

Elongation of the FA carbon chain from C18 to C22 occurs outside the chloroplast by the sequential addition of two C2 moieties from malonyl CoA to a C18 carbon skeleton, a reaction catalyzed by a particulate acyl CoA elongase complex (Stumpf and Pollard, in *High and Low Erucic Acid Rapeseed Oils*, Kramer et al. eds. Academic Press, 1983). Whether the two elongation reactions are carried out by one or two different enzyme complexes is not clear (Taylor et al., *Plant Physiol.* 99:1609–1618 (1992)). The same four reactions described above for the biosynthesis of C18 FAs are involved in the further elongation of C18 in plants: (i) condensation of 18:1 CoA with malonyl CoA to form a β-ketoacyl derivative, (ii) reduction and (iii) dehydration of the β-ketoacyl derivative, and (iv) reduction of the double bond (Creach and Lessire *JAOCS* 70:1129–133 (1993)). However, because of the difficulties in solubilizing membrane-bound enzymes, the elongase complex has not been well characterized. Elongases have been partially purified from several plants, including *Allium porrum* or leek (Bessoule et al., *Arch. Biochem. Biophys.* 268:475484 (1989)), *Lunaria annua* or honesty (Fehling et al., *Biochim. Biophys. Acta* 1126:88–94 (1992)), and *Brassica napus* or rapeseed (Creach and Lessire, 1993, supra).

In Arabidopsis, mutations in a gene associated with fatty acid elongation, the FAE1 gene, result in a deficiency in acyl chain elongation activities from C18 to C20 and C20 to C22, and in highly reduced levels of seed VLCFAs (James and Dooner, *Theor. Appl. Genet.* 80:241–245 (1990); Lemieux et al., *Theor. Appl. Genet.* 80:234–240 (1990); James and Dooner *Theor. Appl. Genet.* 82:409–412 (1991); and Kunst et al. *Plant Physiol. Biochem.* 30:425–4343 (1992)).

FA biosynthetic genes have been isolated by the conventional biochemical approaches of purifying the corresponding enzyme in order to generate antibodies or oligonucleotides with which to probe cDNA libraries. Among them are genes for ACP (Schmid and Ohlrogge, *Plant Mol. Biol.* 15:765–778 (1990)), KASII (International Publications WO92/03564 and WO93/10240), KASIII (Tai and Jaworski, *Plant Physiol.* 103L1361–1367 (1993)), stearoyl-ACP desaturase (International Publication No. WO91/18985), acyl-ACP thioesterases (U.S. Pat. No. 5,298,421) enoyl-ACP reductase (Kater et al., *Plant Molec. Biol.* 17:895–909 (1991)), 3-ketoacyl-ACP reductase (Klein et at., *Mol. Gen. Genet.* 233:122–128 (1992)), acyl-ACP:glycerol-3-P acyl transferase (Weber et al., *Plant Molec. Biol.* 17:1067–1076 (1991)). Others have been isolated on the basis of DNA homology to previously cloned genes from related species, e.g., genes for stearoyl-ACP desaturases (Knutzon et al., *Proc. Natl. Acad. Sci.* USA 89:2624–2628 (1992)) or acyl-ACP:glycerol-3-P acyl transferases (Nishida et al., *Plant Molec. Biol.* 21:267–277 (1993)).

Genes encoding FA biosynthetic enzymes in Arabidopsis have also been isolated. Examples include the FAD3 gene encoding an endoplasmic reticulum (ER) 18:2 desaturase (Arondel et al., *Science* 258:1353–1354 (1992)), FAD3 (Yadav et al., *Plant Physiol.* 103:467–476 (1993)), and the FAD2 gene, which encodes another ER enzyme, an 18:1 desaturase (Okuley et al. *The Plant Cell*, 6:147–158 (1994)).

There have been no reports of the isolation of FAE1 genes. Isolation of these genes would be particularly useful in modulating fatty acid synthesis in plants. These and other advantages are provided by the present invention.

SUMMARY OF THE INVENTION

The present invention provides isolated DNA constructs comprising a polynucleotide sequence from an FAE1 gene. FAE1 genes encode elongation enzymes which catalyze the conversion of C18 FAs to C20–C22 FAs. A preferred embodiment of the genes of the invention comprises sequences substantially identical to sequences which are, which contain, or which are contained within, SEQ. ID. No. 1.

DNA constructs comprising the polynucleotides of the invention are used to modify FAE1 gene expression and thereby modulate FA content in plant organs or parts, particularly seeds. Thus, a DNA construct of the invention may further comprise a promoter operably linked to the polynucleotide sequence. The promoter is preferably a plant promoter such as a seed-specific promoter. If suppression of an endogenous FAE1gene is desired, the polynucleotide sequence may be linked to the promoter in the sense or antisense orientations.

The invention also provides transgenic plants (e.g., Brassica plants) comprising a recombinant expression cassette which includes a plant promoter operably linked to the polynucleotide sequence. The transgenic plants exhibit altered FA content in one or more tissues. For use in plants which produce edible oils, the introduction of the recombinant expression cassettes preferably results in inhibition of an endogenous FAE1 gene, resulting in plants with decreased VLCFA content.

The invention further provides a method of altering FA content in a plant. The method comprises introducing into plant tissue a recombinant expression cassette comprising a plant promoter operably linked to a polynucleotide sequence from an FAE1gene, in the sense or the antisense orientation. The promoter may be a tissue-specific promoter, e.g., a seed-specific promoter. The expression cassette is typically introduced into the plant tissue using Agrobacterium or other standard means. The transformed plant tissue is regenerated into whole plants, whereby normally the regenerated plant transcribes the introduced polynucleotide sequence. The plants are then assayed and selected for altered FA content.

The invention further provides methods of isolating an FAE1 gene from a plant. The method may comprise probing a DNA library (e.g., a cDNA library) prepared from the plant with oligonucleotide probes comprising a polynucleotide sequence from an FAE1 gene.

DEFINITIONS

The phrase "nucleic acid sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The term "promoter" refers to a region of DNA upstream from the start of transcription and involved in recognition and binding of RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants, as well as certain lower plants such as algae. It includes plants of a variety of ploidy levels, including polyploid, diploid and haploid.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

As used herein an "FAE1 gene" is a gene encoding an enzyme, or a component of an enzyme, that catalyzes the conversion of oleic acid (18:1) to eicosenoic acid (20:1) and eicosenoic acid to erucic acid (22:1).

As used herein, a homolog of a particular FAE1 gene (e.g., SEQ. ID. No. 1) is a second gene in the same plant type or in a different plant type, which has a polynucleotide sequence of at least 50 contiguous nucleotides which are substantially identical (determined as described below) to a sequence in the first gene. It is believed that, in general, homologs share a common evolutionary past.

A "polynucleotide sequence from an FAE1 gene" is a subsequence or full length polynucleotide sequence of an FAE1 gene which, when present in a transgenic plant, has the desired effect, for example, inhibiting expression of the endogenous FAE1 gene. In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from an FAE1 gene". In addition, the term specifically includes those full length sequences substantially identical (determined as described below) with an FAE1 gene sequence and that encode proteins that retain the function of the FAE1 enzyme. Thus, the above term includes variant polynucleotide sequences which have substantial identity with the sequences disclosed here and which encode enzymes capable of catalyzing the same reactions described above.

In the case of polynucleotides used to inhibit expression of an endogenous gene, the introduced sequence also need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

BRIEF DESCRIPTION OF THE DRAWINGS

FIG. 4 is a comparison of the amino acid sequences of SEQ. ID. No. 2 and SEQ. ID. No. 4 using the BESTFIT sequence comparison program.

DESCRIPTION OF THE PREFERRED EMBODIMENTS

Figure 1:
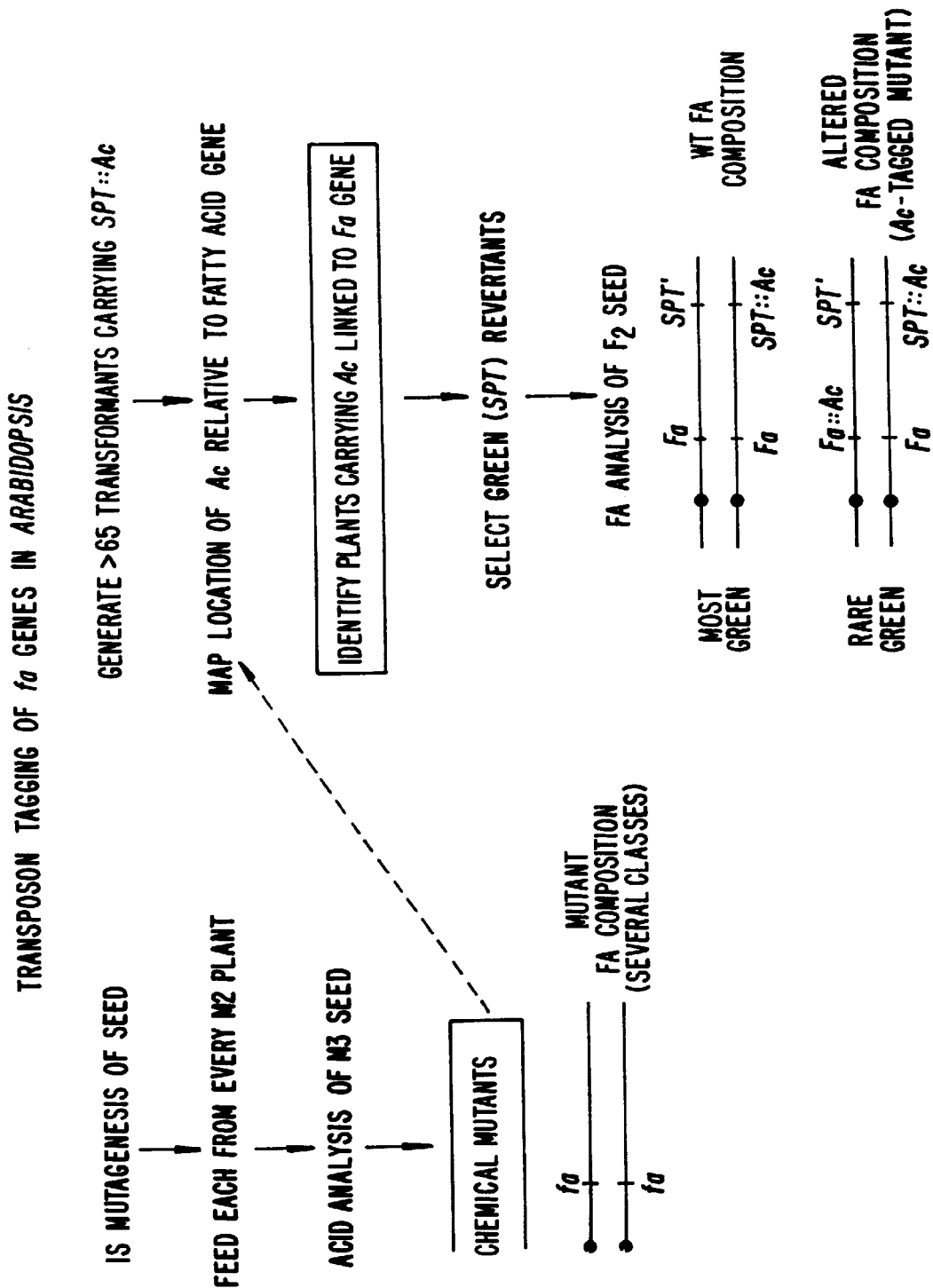
FIG. 1 is an illustration of the strategy used to isolate FA biosynthetic genes from Arabidopsis.

The present invention provides compositions and methods for regulating fatty acid synthesis in plants. The effect of one enzyme, FAE1, on FA synthesis in Arabidopsis has been elucidated by studying mutants of the gene encoding the enzyme. As noted above, a mutant deficient in the elongation of oleate (18:1) and showing only 0.2% eicosenoic acid in its seed oil was described by James and Dooner *Theor. Appl. Genet.* 80:241–245 (1991) and Lemieux et al. *Theor. Appl. Genet.* 80:234–240 (1990). Based on segregation of this trait, James and Dooner and Lemieux et al. determined that it is caused by a single nuclear mutation in a gene that the latter authors designated as FAE1.

The present invention provides cloned genes encoding the FAE1 enzyme. FAE1 genes useful in the present invention include an FAE1 gene identified in Arabidopsis as well as homologs in other plants (either of the same or different genus or species). The present invention also provides recombinant vectors comprising polynucleotide sequences from an FAE1 gene which can be used in variety of ways.

Generally, the invention has use in modulating FA content in all higher plants. The invention thus has use over a broad range of types of plants, including species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browallia, Glycine, Lolium, Zea, Triticum, Sorghum, and Datura.

More specifically, plants for which the invention may be used in modifying FA content include oil crops of the Cruciferae family: canola, res (Brassica spp.), crambe (Crambe spp.), honesty (Lunaria spp.) lesquerella (Lesquerella spp.) and others; the Compositae family :sunflower (Helianthus spp.), safflower (Carthamus spp.), niger (Guizotia spp.) and others; the Palmae family: palm (Elaeis spp.), coconut (Cocos spp.) and others; the Leguminosae family: peanut (Arachis spp.), soybean (Glycine spp.) and others; and plants of other families such as maize (Zea spp.). cotton (Gossypium sp.), jojoba (Simondsia sp.), flax (Linum sp.), sesame (Sesamum spp.), castor bean (Ricinus spp.), olive (Olea spp.), poppy (Papaver spp.), spurge (Euphorbia, spp.) meadowfoam (Limnanthes spp.) and cuphea (Cuphea spp.).

As noted above, VLCFAs, in particular erucic acid, have detrimental nutritional effects and, thus, are undesirable in edible oils. Using standard techniques in plant molecular biology as described below, the production of erucic acid can be decreased in plants used for the production of edible oils, in particular rape, *Brassica napus*.

Alternatively, vegetable oils high in VLCFAs, particularly erucic acid, have many industrial uses. Thus, the invention can be used to increase VLCFA content of plant oils by over-expression of FAE1. In addition, alcohols derived from the VLCFas by reduction of the carboxyl group will also increase in these plants. VLCF alcohols are esterified with VLCFAs in jojoba oil. and can be used as a substitute for sperm whale oil in high quality lubricants and a valuable carrier for medicines. For instance, crambe and jojoba, two sources of industrial oils valued for their VLCFA content, can be modified to increase production of these FAs. The C20–C22 FA content of Crambe seed oil is about 50–60% 22:1 (Salunkhe and Desai, in *Postharvest Biotechnology of Oilseeds* pp 187–197 (CRC Press, Boca Raton, Fla., 1986)) and jojoba seed wax, currently, about 54% 20:1+22:1 (Salunkhe and Desai, supra), could be increased by over-expression of FAE1.

The polynucleotides of the invention can also be used to modify other desirable traits in plants. For instance, since the constitution of leaf surfaces affects their permeability, by changing the composition of the FAs that make up the leaf (surface) cuticular waxes, the drought tolerance of plants can be affected. Thus, any trait in which VLCFA synthesis is important can be altered using the methods of the invention.

FAE1 polypeptides

The enzymes of the invention share homology with those of two other condensing enzymes that utilize malonyl CoA, chalcone synthase (CHS) and stilbene synthase (STS). A consensus sequence among the three enzymes was revealed from a comparison of their amino acid sequences performed with the GCG computer programs (Devereux et al., *Nuc. Acids. Res.* 12:387–395 (1984)). It consists of 17 amino acids spread over a 50 amino acid region close to the carboxyl end of the proteins (staring at position 392 in FAE1). This region is just upstream of the CHS-STS 12 amino acid "signature sequence" Fliegmann et al., *Plant Mol. Biol.* 18:489–503 (1992)), which does not occur in the proteins of the invention.

The FAE1 protein also shares homology with a conserved region in CHS and STS which is close to the active site cysteine identified by Lanz et al., *J. Biol. Chem.* 266:9971–9976 (1991)). However, this region of homology {L-A-K-D-L-X(9)-L-V-V} (SEQ ID NO:5)does not overlap with the consensus sequence for the CHS/STS active site {G-C-(FY)-(GA)-G-G-T-X(2)-R} (SEQ ID NO.:6), but lies immediately next to its carboxyl end.

The amino acid sequence of the proteins of the invention is also homologous to the ketoacyl synthase (KAS) III enzyme of *E. coli* and spinach, the condensing enzyme that initiates FA biosynthesis in bacteria and plants by coupling acetyl CoA to malonyl ACP. In particular, the FAE1 protein disclosed here is 35% identical and 47% similar to the *E. coli* KASIII (encoded by the fabH gene), and 32% identical and 46% similar to a KASIII from spinach over a 57 amino acid stretch that also starts at position 392 of FAE1.

The FAE1 enzymes of the present invention preferably possess catalytic activity which is substantially equal to or higher than the activity of the protein set forth in SEQ. ID. No. 2. The polypeptides of the present invention may be natural, i.e., including an entire native FAE1 enzyme isolated and purified from a natural source, or may be synthetic. Such natural FAE1 polypeptides may be isolated from plant material, using methods described in the scientific literature which has been referenced above. By "isolated," it is meant that the FAE1 proteins have been removed from their native environment, such as the plant tissue where they normally occur. Thus, the term "isolated" is meant to include the presence of a FAE1 polypeptide as a heterologous component of a cell or other system, such as a microorganism expression host or a transformed higher plant. For example, the FAE1 polypeptide of the present invention may be expressed in a microorganism host, such as bacteria or yeast, transformed or transfected with a DNA construct which encodes the polypeptide. Usually, such expression in microorganism hosts will be a first step in producing a "purified" FAE1 polypeptide. Alternatively, "isolated" FAE1 polypeptides may be expressed in transformed higher plants, where the FAE1 polypeptides will frequently not be subjected to any form of purification. Such polypeptides, however, will be isolated in the sense that they have been removed from their native environment, frequently being the result of expression of a heterologous gene, although in some cases being the result of expression of a homologous gene under the control of a heterologous promoter. In the latter case, the homologous FAE1 polypeptide may be expressed in plant tissues and at times other than would normally be the case.

FAE1 polypeptides may be isolated and purified from any natural source possessing significant amounts of a natural or native FAE1 enzyme. Isolation and purification may be obtained by conventional chemical purification techniques, such as liquid chromatography, affinity chromatography, gradient centrifugation, gel electrophoresis, size exclusion chromatography, ion exchange chromatography, hydrophobic interaction chromatography, reversed-phase chromatography, and the like. Such techniques are well described in the scientific and patent literature. See, for example, Scopes, *Protein Purification*, Springer-Verlag, New York (1982). Such techniques are suitable for isolation of FAE1 polypeptides both from natural cellular sources and from recombinantly modified expression hosts, The FAE1 enzymes of the present invention may be obtained in a substantially pure form. By "substantially pure," it is meant that the polypeptide will be present in an intermediate or final composition and a purity of at least about 50%, based on the weight of FAE1 polypeptide present in the total weight of the composition (weight/weight; w/w), and will be substantially free from interfering proteins and contaminants, particularly proteins and contaminants which interfere with the desired catalytic activity and/or which are toxic, immunogenic, or which otherwise prevent the desired use of a final product. Preferably, the FAE1 polypeptides will be isolated or synthesized in a purity of at least about 60% w/w, more preferably at least about 70% w/w, and most preferably at least about 80% w/w. Often, even higher levels of purity may be obtained, with 90% w/w, 95% w/w, or higher usually being achievable. Very high levels of purity, typically above 98% w/w and most preferably above 99% w/w, can also be obtained.

Synthetic FAE1 polypeptides according to the present invention may be produced by either of two general approaches. First, polypeptides having fewer than about 200 amino acids, usually fewer than about 150 amino acids, and preferably fewer than about 100 amino acids, may be synthesized, e.g., by the well known Merrifield solid-phase method where amino acids are sequentially added to a growing chain (Merrifield (1963) *J. Am. Chem. Soc.* 85:2149–2156). Commercial systems employing such solid phase techniques for the automated synthesis of polypeptides are available from vendors, such as Applied Biosystems, Inc., Foster City, Calif.

The second and generally preferred method for synthesizing FAE1 polypeptides according to the present invention involves the expression in cultured cells of recombinant DNA molecules encoding all or a desired portion of a FAE1 protein. The recombinant DNA molecule may incorporate either a natural or synthetic gene, with natural genes and cDNA being obtainable from plant seed material by conventional methods, as described in the literature cited above. The isolation of polynucleotides encoding a desired FAE1 is described in detail below.

Polynucleotides encoding FAE1

The Example section below, which describes the isolation and characterization of an FAE1 gene in Arabidopsis is exemplary of a general approach for isolating genes of the invention. Isolation of this gene allows one of skill to readily isolate homologous genes in Arabidopsis and other plant species. The isolated genes can then be used to construct recombinant vectors for altering FAE1 gene expression in transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of FAE1 genes may be accomplished by a number of techniques. For instance, transposon tagging of an FAE1 gene can assist in the isolation of the relevant gene. Transposon tagging involves introducing a transposon into the plant which leads to a mutation of the target gene and a detectable phenotypic change in the plant. Using a probe for the transposon, the mutant gene can then be isolated. Using the DNA adjacent to the transposon in the isolated mutant gene as a probe, the normal wild type allele of the target gene can be isolated. See, e.g., Haring, et al., *Plant Mol. Biol.* 16:449469 (1991) and Walbot, *Ann. Rev. Plant Mol. Biol.* 43:49–82 (1992). As shown below, a particularly useful transposon tagging system is that disclosed in U.S. Pat. No. 5,013,658.

An alternative method uses oligonucleotide probes to identify the desired gene in a cDNA or genomic DNA library. To construct genomic libraries, large S segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as a seed, and a cDNA library which contains the FAE1gene transcript is prepared from the mRNA. Alternatively, cDNA may be prepared from mRNA extracted from other tissue types (organs) in which FAE1 genes or homologs are expressed such as seeds, fruits, leaves, stems, and roots.

The cDNA or genomic library can then be screened using a probe based upon the sequence of a cloned FAE1 gene such as that shown in SEQ. ID. No. 1. Probes may be used to hybridize with genomic DNA or cDNA sequences to isolate homologous genes in the same or different plant species. The use of such hybridization techniques for identifying homologous genes is well known in the art and need not be described further.

Alternatively, polynucleotides may be synthesized by well-known techniques as described in the technical literature. See, e.g., Carruthers et al., *Cold Spring Harbor Symp. Quant. Biol.* 47:411418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The isolated sequences prepared as described herein, can be used in a number of techniques to suppress endogenous FAE1 gene expression (i.e., to inhibit elongation of C18 FAs to C20 and C22). For instance, antisense technology can be conveniently used to inhibit FAE1 gene expression. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous FAE1 gene or genes to be repressed. The sequence, however, need not be perfectly identical to inhibit expression. The vectors of the present invention can be designed such that the inhibitory effect applies to other proteins within a family of genes exhibiting homology or substantial homology to the target gene. For example, suppression of the FAE1 gene shown in SEQ. ID. No. 1 may serve to impose the same suppressive effect on other FAE1 genes with sufficient identity. Similarly, segments from FAE1 genes from Arabidopsis can be used to inhibit expression of homologous genes in related plant species such as member of the genus Brassica or as a means to obtain the corresponding sequences to be used to suppress the endogenous Brassica gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of FAE1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585–591 (1988).

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Isolated sequences prepared as described herein can also be used to introduce FAE1 expression or to enhance or increase endogenous FAE1 gene expression (i.e., to increase production of VLCFAs). Where overexpression of the FAE1 gene is desired, an FAE1 gene from a different species may be used to decrease potential sense suppression effects. For instance, the Arabidopsis FAE1 gene can be used to increase expression in Brassica.

One of skill will recognize that the polypeptides encoded by the FAE1 genes, like other proteins, have different domains which perform different functions. Thus, the FAE1 gene sequences need not be full length, so long as the desired functional domain of the protein is expressed. Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

To use isolated FAE1 sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421477 (1988). A DNA sequence coding for the desired FAE1 polypeptide, for example a cDNA sequence encoding a full length protein, will preferably be combined with transcriptional and translational initiation regulatory sequences which will direct the transcription of the sequence from the FAE1 gene in the intended tissues of the transformed plant.

For example, for overexpression, a plant promoter fragment may be employed which will direct expression of FAE1 in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the FAE1 gene in a specific tissue or may be otherwise under more precise environmental or developmental control. Such promoters are referred to here as "inducible" promoters. Examples of environmental conditions that may effect transcription by inducible promoters include anaerobic conditions, elevated temperature, or the presence of light.

Examples of promoters under developmental control include promoters that initiate transcription only in certain tissues, such as fruit, seeds, or flowers. For example, the use of a napin promoter of *Brassica napus* (Lee et al. *Proc. Natl. Acad. Sci. USA* 88:6181–6185 (1991)) or the promoter from the Arabidopsis FAE1 gene can direct expression of the FAE1 polypeptide in seed.

If proper polypeptide expression is desired, a polyadenylation region at the 3'-end of the FAE1 coding region should be included. The polyadenylation region can be derived from the natural gene, from a variety of other plant genes, or from T-DNA.

The vector comprising the sequences from an FAE1 gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desire plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional Agrobacterium tumefaciens host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:7073 (1987).

*Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired FAE1-controlled phenotype. Such regeneration techniques rely on manipulation of certain phytohormones in a tissue culture growth medium, typically relying on a biocide and/or herbicide marker which has been introduced together with the FAE1 nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467486 (1987).

The methods of the present invention are particularly useful for incorporating the FAE1 genes into transformed plants in ways and under circumstances which are not found naturally. In particular, the FAE1 polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of FAE1 gene expression is conveniently detected by analyzing FA content of plant material from the desired plant. Briefly, lipids are extracted from the plant material (e.g., seeds), FAs are cleaved from the triacylglycerol, and analyzed by gas chromatography as described for instance in James and Dooner *Theor. Appl. Genet.* 80:241–245 (1990). In addition, antisense or sense suppression of the endogenous gene can be detected by reduction of mRNA levels as measured by, for instance, Northern blots.

Plant suppressants of the invention have lower levels of erucic acid less than about 2% (of total FA seed content), preferably lower than about 1%, more preferably lower than about 0.5%, and most preferably lower than about 0.1%. Overexpressing plants of the invention have levels of erucic acid substantially higher than the corresponding untransformed plant, e.g., at least 10% higher, preferably at least 20% higher, more preferably at least 30% higher, and most preferably at least 40% or 50% higher. Preferred resultant levels of erucic acid in overexpressing Brassica plants of the invention are at least about 40% (of total FA seed content), preferably at least about 50%, more preferably at least about 60%. Even higher levels may be obtained with other oil producing plants, e.g., in order of increasing preference at least about 70%, 80% or 90%. Erucic acid may be extracted from overexpressing plants of the invention using known methods. See Salunkhe and Desai (1986), supra.

The following Examples are offered by way of illustration, not limitation.

EXAMPLE 1

Isolation and Sequencing of the FAE1 Gene from Arabidopsis

The strategy used to isolate FA biosynthetic genes from Arabidopsis is illustrated in FIG. 1. In this work, transposon tagging was done with the autonomous maize element Ac.

A. Mutant creation and Ac transformation

1. Mutant Formation

A collection of mutants was induced and characterized in order to genetically define loci that affect FA composition in Arabidopsis seeds (obtainable from the Arabidopsis Biological Resource Center at Ohio State University) as described by James and Dooner (1990), supra.

2. Ac transformation 68 independent single locus Arabidopsis transformants carrying Ac in the T-DNA were generated using the methods of Keller et al., *Genetics*, 131:44–459 (1992). This number provides >95% confidence that any gene in the Arabidopsis genome will be no farther than 15 cM from an introduced Ac, assuming random integration of the T-DNA in the genome and a <600 cM genetic map (Koorneeff et al., in *Genetic Maps*, S. J. O'Brien ed. (Cold Spring Harbor Press, Cold Spring Harbor (1992)). In Arabidopsis, as well as in maize and other organisms, transposons of the Ac/Ds family transpose preferentially to sites linked to the donor site (Keller et al., *Theor. Appl. Genet.* 86:585–588 (1993)).

Therefore, in order to tag a specific gene, it is preferable to initiate the tagging experiment with an Ac (or Ds) element linked to the gene of interest. This approach, referred to as directed tagging, requires mapping of the T-DNAs relative to the target loci. Scoring for the presence or absence of the T-DNA was facilitated by the Hyg-R (hygromycin resistance) transformation marker. The number of plants with transposed Ac (trAc) elements required to isolate a specific FA mutation was therefore greatly reduced relative to that required in a random transposon tagging approach.

3. T-DNA localization (mapping)

Of twenty-four T-DNAs localized to one of the five Arabidopsis chromosomes, three were linked to FAE1. In transformants K805, B116, and C231, the T-DNAs were located respectively, 15, 22, and 40 cM from FAE1. FAE1 is loosely linked to the RFLP marker 518 which was mapped to chromosome 4 by Chang et al., *Proc. Natl. Acad. Sci. USA* 85:6856–6860 (1988). Linkage of the BI 16 T-DNA to marker 518 was confirmed by a bulked segregant analysis procedure (Michelmore et al., *Proc. Natl. Acad. Sci. USA* 88:9828–9832 (1991)) in which paired DNA samples obtained from pooled homozygous Hyg-R/Hyg-R and +/+ segregants from a Hyg-R/+ (WS×Columbia) heterozygote were scored for segregating RFLPs. A chromosomal location was assigned to 24 single locus, Ac-containing T-DNA insertions by the combination of two-point crosses and bulked segregant analyses.

4. Make up of T-DNA

In the pJJ4404 construct used in the derivation of transgenic line B116, Ac lies in the 5' untranslated region of the SPT (streptomycin phosphotransferase) gene (Jones et al., *Science* 244:204–207 (1989); Keller et al., *Plant Mol. Biol.* 21:157–170 (1993)). Somatic excisions of Ac during the development of the cotyledons can be detected as green sectors on a white background in Arabidopsis seedlings germinated in streptomycin. Germinal excisions of Ac give rise to SPT' fully green seedlings, about half of which carry a trAc element somewhere in the genome (Dean et al., *The Plant Journal* 2:69–81 (1992); Keller et al., *Genetics* 131:449–4591(1992)). Therefore, SPT::Ac constitutes an efficient marker for selecting plants that have undergone transposition.

Germinal selections recovered from one plant may derive from a common premeiotic event and carry the same transposed element. To avoid extensive sampling of duplicates for the same transposition event, in general, no more than four green seedling selections from any one plant were transferred to the greenhouse.

B. Identification of a new fae1 mutation

1. Isolation and characterization of germinal selections

Green SPT' seedling were selected on streptomycin (Jones et al., (1989), supra) grown to maturity in the greenhouse, and the PA composition of their seeds was analyzed by gas chromatography (GC) as described previously (James and Dooner (1990), supra). Because fae1 and several other mutations affecting seed FA composition are codominant (James and Dooner (1990); Lemieux et al., (1990), supra) they can be identified in the heterozygous condition, a clear advantage when dealing with a difficult phenotype, such as a chromatographic profile. Selections were made from lines in which Ac was either linked or unlinked to FAE1. Table 1 gives the number of SPT' selections analyzed, the number of plants which produced them, and the location of Ac relative to FAE1 in each line. Also given are estimates of the minimum and maximum number of independent Ac reinsertions screened, assuming a 50% Ac reinsertion frequency (Keller et al. (1992), supra).

The minimum number, i.e., the number screened if all the green sibs were derived from the same transposition event, corresponds to half the number of parent plants which produced green seedlings. The maximum number, i.e., the number screened if all the sibs resulted from independent transposition events, corresponds to half the number of selections analyzed. The actual number of independent Ac reinsertions assayed lies somewhere between the two values since both clonal and single Ac transposition events can be recovered from the same plant (Keller et al, 1992).

TABLE 1

SPT' revertants analyzed for fatty acid composition

| T-DNA line | Ac-Fae1 linkage | No. SPT' selections analyzed | No. plants producing selections | Min.–Max. No. independent Ac reinsertions[a] |
|---|---|---|---|---|
| K805 | 15 cM | 1522 | 660 | 330–761 |
| B116 | 22 cM | 721 | 272 | 136–361 |
| Subtotal | Linked | 2243 | 932 | 466–1122 |
| C201 | Unlinked | 2107 | 324 | 162–1054 |
| B246 | Unlinked | 680 | 227 | 114–340 |
| A018 | Unlinked | 273 | 91 | 45–136 |
| Subtotal | Unlinked | 3060 | 642 | 321–1530 |

[a]Assumptions: 50% reinsertions among SPT' selections. Minimum, all selections clonal. Maximum, all selections independent.

2. Identification of Fae1-G309

A total number of 721 SPT' selections from B116 were analyzed. Plants from the B116 line produced an average of >1% green selections per plant, but S the percentages varied greatly from plant to plant. One selection, G309, produced seed with the reduced 20:1 content typical of an FAE1/fae1 heterozygote. Upon selfing, one quarter of its progeny had a more extreme seed FA composition, indistinguishable from that of the EMS-induced mutant fae1-2 (referred to as 9A1 in James and Dooner, 1990). The new mutation was tested for allelism with fae1-2. Because the mutants failed to complement, the provisional designation fae1-G309 was assigned to the new mutant. The FA compositions of fae1-G309 homozygous, heterozygous and wild-type seeds are presented in Table 2A; those of fae1-2 and fae1-2/fae1-G309 seeds, in Table 2B.

TABLE 2

Percent fatty acid composition of seeds from various genotypes

| Sample | 16:0 | 18:0 | 18:1 | 18:2 | 18:3 | 20:0 | 20:1 | 22:1 |
|---|---|---|---|---|---|---|---|---|
| A. | | | | | | | | |
| Wild type (+/+) | 5.1 | 1.6 | 10.9 | 31.2 | 20.6 | 1.5 | 24.2 | 2.3 |
| fae1/G309/+ | 5.9 | 2.2 | 19.1 | 33.6 | 21.2 | 0.9 | 14.5 | 1.0 |
| fae1/G309/ fae1/G309 | 6.4 | 2.4 | 26.1 | 38.7 | 25.3 | 0.4 | 0.1 | 0.0 |
| B. | | | | | | | | |
| fae1-2/fae1-2 | 8.5 | 2.9 | 30.8 | 30.1 | 26.9 | 0.0 | 0.4 | 0.0 |
| fae1-2/ fae1/G309 | 6.6 | 2.5 | 32.9 | 33.4 | 22.8 | 0.6 | 0.7 | 0.0 |

C. Evidence that the new fae1 mutation is tagged by Ac

1. Cosegregation of the fae mutant phenotype with an Ac-hybridizing band

DNA analysis of the fae1-G309 derivative showed the presence of a new Ac-hybridizing band. DNA extraction and DNA blot analysis were performed as previously described (Keller et al. (1992), supra). The joint segregation of this new Ac band with the fae1 mutation was tested in the self progeny of an fae1-G309/Fae1 heterozygote. Segregating individuals were scored as Fae1/Fae1, Fae1/fae1 or fae1/fae1 by GC analysis of their seed FA composition and as Ac/(−) or +/+ by DNA gel blot analysis. Thus, six genotypic classes could be distinguished. DNA from 54 individuals was digested with HindIII and hybridized with a probe from the 5' end of Ac (Kunze et al., EMBO J. 6:1555–1563 (1987)). Results of these hybridizations showed two Ac-hybridizing bands segregating in the progeny, a 3.3-kb and a 2.4-kb band. The former represents the newly transposed Ac (trAc) and the latter, the Ac at the SPT::Ac resident site in the T-DNA (the selfed parent was the original G309 green selection, SPT'/SPT::Ac).

The results of the cosegregation analysis are presented in Table 3A. All of the individuals carrying the new trAc were either homozygous or heterozygous for the new fae1 mutation. Conversely, all of the individuals that lacked the trAc were wild-type. Therefore, no recombinants were recovered (linkage $X^2$=54, P<0.001).

DNA from the region flanking the 5' end of the trAc in the fae1-m1 (Ac) mutant was generated for cloning by inverse PCR (Ochman et al., Genetics 120:621–623 (1988)). DNA was obtained from progeny of fae1-G309 that contained the 3.3-kb Ac-hybridizing HindIII fragment that cosegregated with the fae1 phenotype, but lacked the smaller 2.4-kb Ac-hybridizing band. Approximately 0.5 ug of genomic DNA was digested with HindIII and ligated overnight at 16° C. under dilute conditions (200 ul reaction volume) to favor circularization of the HindIII fragments. Primers FL125, oriented outward from the 5' end of Ac (CGGTTATACGATAACGGTCG) (SEQ ID NO.:7) and JK30, just 5' from the first HindIII site in Ac (GTACGATGAAGTGGTTAGCC) (SEQ ID NO.:8) were used to amplify the 1.5-kb of genomic DNA flanking the 5' end of the trAc.

This flanking DNA was used to reprobe the same DNA gel blots. As expected, the new probe detected the same 3.3-kb Ac-homologous fragment and, in addition, a new fragment of about 1.8 kb. If Ac had, in fact, tagged the FAE1 gene, all the segregating fae1 mutant plants should be homozygous for the 3.3-kb band, all Fae1/fae1 plants should be heterozygous for the 3.3-kb and the 1.8-kb band and all wild-type plants should be homozygous for the 1.8-kb band. The results of the analysis are presented in Table 3B. 53 of the 54 segregants fit the expectation. The one exception (segregant #5) was heterozygous for the 3.3-kb trAc band. There are two plausible explanations for this exception. (1) The new fae mutation is not tagged by the trAc, but is closely linked to it, and this individual is a recombinant between the fae1 mutation and the trAc. (2) The new fae1 mutant is tagged by the trAc and this individual is the product of an Ac excision that did not restore gene function. Segregant #5 also had a new Ac-hybridizing band, which was absent in the other 53 sibs (data not shown), an observation suggesting that it might have originated by secondary transposition of Ac.

TABLE 3

Segregation data for the self-progeny of a
Fae1/fae1; trAc/ + heterozygote

A. DNA from segregants scored with an Ac probe

| FAE1 genotype | trAc genotype | | |
|---|---|---|---|
| | trAc/(−) | +/+ | Total |
| Fae1/Fae1 | 0 | 9 | 9 |
| Fae1/fae1 | 29 | 0 | 29 |
| fae1/fae1 | 16 | 0 | 16 |
| | 45 | 9 | 54 |

B. DNA from segregants scored with probes for Ac and the flanking DNA

| FAE1 genotype | trAc genotype | | | |
|---|---|---|---|---|
| | trAc/trAc | trAc/+ | +/+ | Total |
| Fae1/Fae1 | 0 | 0 | 9 | 9 |
| Fae1/fae1 | 0 | 29 | 0 | 29 |
| fae1/fae1 | 15 | 1 | 0 | 16 |
| | 15 | 30 | 9 | 54 |

2. Reversion of the fae1 mutant

To confirm that the fae1-G309 mutation was tagged by Ac, progeny of mutant plants were screened for putative revertants, i.e., individuals with an intermediate seed FA composition, which could then be examined for excision of Ac from the cloned DNA. A total of 1052 offspring from four fae1-G309 plants were screened and three putative revertants to wild-type were identified on the basis of an intermediate seed FA composition, typical of Fae1/fae1 heterozygotes (12–15% 20:1). Using DNA gel blot analysis, all three exceptions were found to be heterozygous for the 3.3-kb band in the original mutant allele and a 1.8-kb wild-type-sized band. This is the result expected if these individuals originated from Ac excision events that restored gene function.

The DNA around the trAc insertion site in the wild-type progenitor allele, the fae1-G309 mutant, and the three putative revertants was amplified by the polymerase chain reaction procedure described in Saiki (1990) and sequenced. DNA was sequenced with either the Sequences kit (U.S. Biochemical) or the fmol kit (Promega) following the recommendations of the manufacturers. A comparison of the sequences is presented in FIG. 2.

In general, when Ac excises it leaves behind an 8 bp "footprint" with occasional deletion or addition of bases to restore the reading frame number (a multiple of three). However, somewhat unexpectedly, the DNA sequences of the three putative revertants were identical to that of the wild-type progenitor. The sequence of the putative FAE1 protein around the site of insertion of Ac may be intolerant of amino acid changes, so that only the rare events that restore not just the correct reading frame but the original sequence are selected as revertants. If so, segregant #5, the exception from the cosegregation analysis (Table 3B) would represent an Ac excision event that did not restore the original amino acid sequence and, thus, failed to restore gene function. The DNA sequence of segregant #5 (FIG. 2) revealed an 8bp footprint at the Ac excision site, indicating that this exception had originated by an Ac excision that created a frame-shift mutation and knocked out gene function.

Thus, the analysis of revertants and of the one null exception in the cosegregation test confirms that the fae1-G309 mutant arose by insertion of Ac into the FAE1 gene, that it is unstable, and that it can give rise to new alleles at the FAE1 locus. Hence, it has been given the official designation fae1-m1(Ac) to denote that it is the first mutable allele of the FAE1 locus isolated and that it arose by insertion of the transposon Ac.

D. Function of the FAE1 gene in Arabidopsis

1. Expression of FAE1 in developing seed

Since VLCFAs accumulate in seeds, but not in leaves of Arabidopsis (Lemieux et al. (1990), supra), FAE1 should be expressed preferentially in seeds. Expression of the FAE1 gene was assayed by gel blot analysis of RNA from several tissues: leaf, immature seeds and immature siliques plus seeds (pools of ~1 week and of 2–3 week old siliques). RNA from various Arabidopsis tissues (developing siliques, leaves, and immature seed ) was isolated by the phenol-SDS method described in Napoli et al., *The Plant Cell* 2:279–289 (1990), separated by formaldehyde agarose gel electrophoresis and blotted to Duralon-UV membranes (Stratagene). FAE1 transcripts were found to accumulate in siliques containing developing seeds and seeds, but not in leaves.

2. Isolation and sequencing of an FAE1 cDNA clone

The 1.5 Kb FAE1 IPCR fragment was used as a probe to isolate 2 lambda clones from a genomic library of DNA from Arabidopsis, ecotype Ws, partially digested with Sau 3A and ligated into lambda-DASH (Stratagene) using procedures recommended by the manufacturer. The FAE1 gene was localized with in the lambda clones by restriction analysis and by using subcloned regions as probes against silique RNA.

Poly(A) RNA was isolated from 1 g of 2–3 week old green siliques using a Poly ATract system 1000 kit (Promega), following the instructions of the manufacturer. An immature silique cDNA library was made from polyA RNA using the lambda-Zap cDNA synthesis kit (Stratagene), following the instructions provided by the manufacturer. A 1.0 Kb BglII to HindIII fragment from the 5' end of the FAE1 gene and a 700 bp BstXI to EcoRI fragment from the middle of the FAE1 gene were used as probes to screen this cDNA library. A cDNA clone containing a 1.7-kb insert, roughly the size of the FAE1 transcript was isolated and sequenced. DNA was sequenced with either the Sequenase kit (U.S. Biochemical) or the fmol kit (Promega) following the recommendations of the manufacturers.

Figures 2, 3:
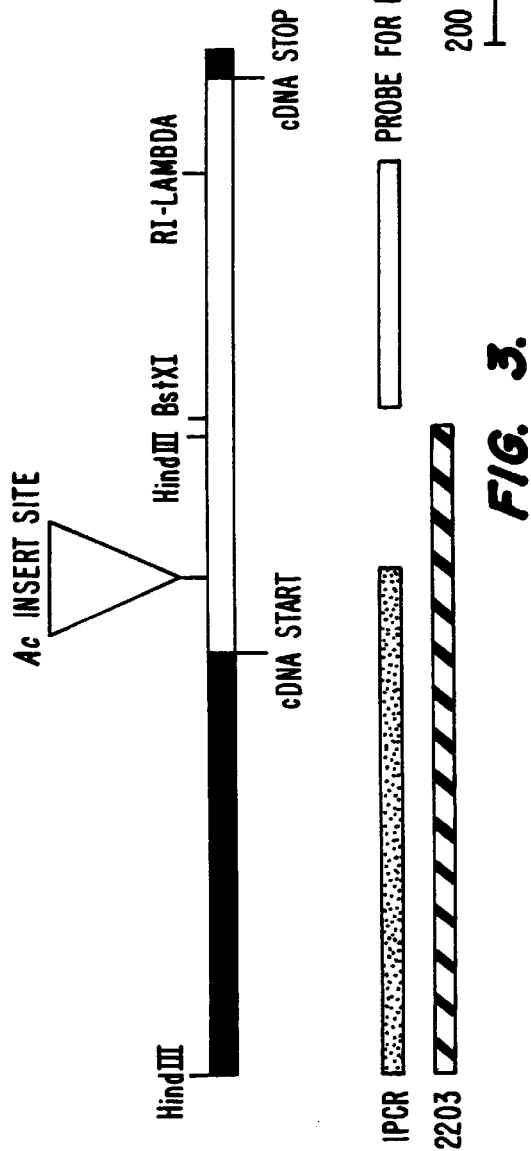
FIG. 2 shows a comparison of the nucleotide sequence of FAE1 around the site of insertion of the transposable element Ac.
FIG. 3 is a diagram of the structure of the FAE1 genomic region, including the location of the cDNA and of the Ac insertion site in fae1-m1(Ac).

The cDNA nucleotide sequence is provided in SEQ. ID. No. 1. It matches the sequence of the genomic DNA throughout its length, indicating that there are no introns in this segment of the FAE1 gene. The cDNA contains a long open reading frame (ORF), but appears to be short of full length. If the ATG located in the corresponding FAE1 genomic sequence 20 nucleotides upstream from the 5' end of the cDNA is the initiation codon, the extended open reading frame encodes a protein of 507 amino acids with a predicted sequence as shown in SEQ. ID. No. 2. A diagram of the structure of the FAE1 genomic region, including the location of the cDNA and of the Ac insertion site in fae1-m1(Ac) is shown in FIG. 3.

EXAMPLE 2

Cloning of FAE1 c-DNA from Brassica napus Immature Embryos

A c-DNA library from *B. napus* (var. Bridger) embryos was constructed in the vector lambda Uni-Zap XR (Stratagene) from 5 μg of polyA RNA following the instructions of the manufacturer. The library was screened for FAE1 clones as follows. A total of 120,000 plaques were screened in duplicate using, respectively, the 3' and 5' ends of the FAE1 genomic fragments from *Arabidopsis thaliana*. Hybridization and washes were done at 60° C. The wash solution was 0.2× SSC and 1% SDS. From the primary screen, a total of 14 potential FAE1 clones hybridizing to either the 3' end probe only or both the 3' and 5' ends were picked for further purification. On secondary screening, four of the original 14 gave positive signals to both probes. Those four clones were purified to homogeneity. They were designated as 3B, 4A, 11A and 12B.

The c-DNA fragments from the four clones were excised from the lambda Zap (Stratagene) vector as plasmids and DNA preps were made. They were characterized with respect to restriction digests, PCR and partial sequencing. Hindi restriction digests of the four clones and of an Arabidopsis c-DNA control showed that the four Brassica clones were different from the Arabidopsis one. While the Arabidopsis clone gave rise to two HIII fragments, three of the Brassica clones yielded only one HIII fragment. Brassica clone 11A gave two HIII fragments, but the fragment sizes were different from those produced by the Arabidopsis FAE1 cDNA clone. Restriction with HIII and XhoI showed that clone 12B was different from 3A and 4A. PCR amplification of 3A and 11A with primers based on the Arabidopsis FAE1 genomic sequence produced different sized bands, confirming the nonidentity of these clones. Partial sequences of 3A and 11A showed that they were 95% homologous at both the 3' and 5' ends of the nucleotide sequence. Sequence I.D. No. 3 is a partial sequence of the coding region of clone 4A, starting with a base pair which is approximately 900 bp downstream of the translation start. Sequence I.D. No. 4 shows the corresponding amino acid sequence. FIG. 4 shows a comparison of this amino acid sequence with a corresponding sequence from the Arabidopsis protein (Seq. I.D. No. 2). This comparison revealed 94% similarity between the two proteins.

EXAMPLE 3

Suppression of FAE1 Expression in Brassica

The Fae1 cDNA, described in Example 1 (SEQ I.D. No. 1) of length 1639 bp, is excised from the vector as an EcoRI/XhoI fragment and cloned into plasmid p2104-CABL (Harpster et al., *Mol. Gen. Genet.* 212: 182–190) that has been digested with Nco I and Bam HI. All restriction sites are treated with Klenow to blunt end them. Standard molecular biology techniques are used (see, e.g., Sambrook et al., supra). Plasmid p2104-CABL has 1.34 kb of CaMV 35S promotor sequence, 60 bp of petunia CABL22 untranslated leader sequence and 260 bp of NOS 3' polyadenylation sequence. With this ligation p35S-Fae1-NOS 3' is selected with Fae1 in the transcriptional orientation for sense suppression and p35S-Fae1-NOS 3' is selected for antisense suppression.

The gene fusions in p35S-Fae1-NOS 3' and p35S-leaF-NOS 3' are excised as Bgl II/Hind III fragments and cloned into the binary vector WTT2143 using standard techniques (Sambrook et al., supra). WM 2143 has a p2'-HPT-NOS 3' fusion for selection of transformed plants and a tetracycline resistance gene for selection of the plasmid in *E. coli* and Agrobacterium.

The resulting binary vectors are mobilized into *Agrobacterium tumefaciens*, strain LBA4404 by conjugation (Herrera-Estrella and Simpson in C. H. Shaw (Ed) *Plant Molecular Biology* pp. 131–158.(1988)).

The sense and/or antisense Fae1 binary constructs are introduced from the Agrobacterium strain carrying them into 5-day old hypocotyl sections of *Brassica napus* cv. Westar by cocultivation. Transformed shoots are selected in the presence of hygromycin B. The Agrobacterium is selected against with 500 mg/ml cefotaxim and the transformed tissue is allowed to callus in the presence of 20 mg/ml hygromycin B, 3% sucrose, 0.2 mg/L 2,4 D and 3 mg/L kinetin. Shoots are stimulated on the transformed callus using medium containing 2.5 uM IBA, 5 mg/L $AgNO_3$, 15 uM thidiazuron and 20 mg/L hygromycin B. The shoots are normalized in medium containing 0.125 mg/L BAP and 500 mg/L Geopen, and then rooted in the absence of hormones and hygromycin B.

Transformed plants are grown to maturity and allowed to self-pollinate. The resulting seeds are analyzed by gas chromatography (as described in Example 1 and references therein) to select for plants with reduced erucic acid content of less than 1% (of total FA content).

EXAMPLE 4

Overexpression of FAE1 in Brassica napus

Overexpression of Fae1 is obtained using the steps of Example 3 with modifications as stated below. The desired outcome is that the seeds of the transgenic plants should have a higher erucic acid content than seeds of the untransformed controls. The constructions in Example 3 do not give translationally active gene products. Translational activity is important for overexpression. Proper design of the p35S-Fae1-NOS 3' fusion is achieved by using standard oligonucleotide mutagenesis techniques (Sambrook et al., supra ) to create an Nco I site at the starting methionine in the genomic clone of Fae1 and then fusing this and the bulk of the gene from the cDNA to the 35S promoter at the Nco I site in plasmid 2104-CABL. After transformation, plant growth, self-pollination and gas chromatograph analysis, as called for in Example 3, plants are selected with erucic acid content of at least 40% (of total FA content).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated DNA construct comprising a polynucleotide at least about 150 nucleotides in length and having a sequence at least about 80% identical to SEQ. ID. No. 1 or the complement thereof, wherein sequence identity is determined by the Needleman and Wunsch algorithm using standard parameters.

2. The DNA construct of claim 1, wherein the polynucleotide has the sequence of SEQ. ID. No. 1.

3. The DNA construct of claim 1, further comprising a promoter operably linked to the polynucleotide.

4. The DNA construct of claim 3, wherein the polynucleotide is linked to the promoter in an antisense orientation.

5. The DNA construct of claim 3, wherein the promoter is a plant promoter.

6. The DNA construct of claim 5, wherein the promoter is a seed-specific promoter.

7. A transgenic plant comprising a recombinant expression cassette comprising a plant promoter operably linked to a polynucleotide at least about 150 nucleotides in length and having a sequence at least about 80% identical to SEQ. ID. No. 1, wherein sequence identity is determined by the Needleman and Wunsch algorithm using standard parameters.

8. The transgenic plant of claim 7, wherein the plant promoter is a heterologous promoter.

9. The transgenic plant of claim 7, wherein the polynucleotide is linked to the promoter in an antisense orientation.

10. The transgenic plant of claim 7, wherein the plant is *Brassica napus*.

11. The transgenic plant of claim 7, wherein the polynucleotide has the sequence of SEQ. ID. No. 1.

12. A method of increasing very long chain fatty acid content in a plant, the method comprising:

introducing into plant tissue a recombinant expression cassette comprising a plant promoter operably linked to a full-length polynucleotide having a sequence at least about 80% identical to SEQ ID No:1, wherein sequence identity is determined by the Needleman and Wunsch algorithm using standard parameters;

regenerating the plant tissue into a whole plant, whereby the regenerated plant transcribes the polynucleotide; and selecting plants having an increased content of very long chain fatty acids.

13. The method of claim 12, wherein the plant tissue is from Brassica.

14. The method of claim 12, wherein the recombinant expression cassette is introduced into the plant tissue using Agrobacterium.

15. The method of claim 12, wherein the polynucleotide is linked to the promoter in a sense orientation.

16. The method of claim 12, wherein the polynucleotide has the sequence of SEQ. ID. No. 1.

17. The method of claim 12, wherein the promoter is a seed-specific promoter.

18. An isolated polynucleotide which encodes a polypeptide having the sequence of SEQ. ID. No. 2.

19. The DNA construct of claim 1, wherein the polynucleotide has the sequence of SEQ. ID. No. 3 or the complement thereof.

20. A recombinant DNA molecule comprising a plant promoter operably linked to a polynucleotide sequence at least about 150 nucleotides in length and having a sequence at least about 80% identical to SEQ. ID. No. 1, wherein sequence identity is determined by the Needleman and Wunsch algorithm using standard parameters and wherein the plant promoter is heterologous to the polynucleotide sequence.

21. The recombinant DNA molecule of claim 20, wherein the polynucleotide has the sequence of SEQ. ID. No. 1.

22. A recombinant expression cassette comprising a plant promoter operably linked to a polynucleotide sequence at least about 150 nucleotides in length and having a sequence at least about 80% identical to SEQ. ID. No. 1, wherein sequence identity is determined by the Needleman and Wunsch algorithm using standard parameters and wherein the plant promoter is heterologous to the polynucleotide sequence.

23. The recombinant expression cassette of claim 22, wherein the polynucleotide has the sequence of SEQ. ID. No. 1.

24. The recombinant DNA molecule of claim 20, wherein the polynucleotide has the sequence of SEQ ID NO:3.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 1641 base pairs
       (B) TYPE: nucleic acid
       (C) STRANDEDNESS: both
       (D) TOPOLOGY: both (ii) MOLECULE TYPE: cDNA (ix) FEATURE:
       (A) NAME/KEY: misc_feature
       (B) LOCATION: 1..1641
       (D) OTHER INFORMATION: /product= "FAE1 from Arabidopsis"

(xi) SEQUENCE DESCRIPTION: SEQ ID NO:1:

| | | | | | |
|---|---|---|---|---|---|
| ATGACGTCCG | TTAACGTTAA | GCTCCTTTAC | CGTTACGTCT | TAACCAACTT | TTTCAACCTC | 60 |
| TGTTTGTTCC | CGTTAACGGC | GTTCCTCGCC | GGAAAAGCCT | CTCGGCTTAC | CATAAACGAT | 120 |
| CTCCACAACT | TCCTTTCCTA | TCTCCAACAC | AACCTTATAA | CAGTAACTTT | ACTCTTTGCT | 180 |
| TTCACTGTTT | TCGGTTTGGT | TCTCTACATC | GTAACCCGAC | CCAATCCGGT | TTATCTCGTT | 240 |
| GACTACTCGT | GTTACCTTCC | ACCACCGCAT | CTCAAAGTTA | GTGTCTCTAA | AGTCATGGAT | 300 |
| ATTTTCTACC | AAATAAGAAA | AGCTGATACT | TCTTCACGGA | ACGTGGCATG | TGATGATCCG | 360 |
| TCCTCGCTCG | ATTTCCTGAG | GAAGATTCAA | GAGCGTTCAG | GTCTAGGTGA | TGAGACGTAC | 420 |
| AGTCCTGAGG | GACTCATTCA | CGTACCACCG | CGGAAGACTT | TGCAGCGTC | ACGTGAAGAG | 480 |
| ACAGAGAAGG | TTATCATCGG | TGCGCTCGAA | AATCTATTCG | AGAACACCAA | AGTTAACCCT | 540 |
| AGAGAGATTG | GTATACTTGT | GGTGAACTCA | AGCATGTTTA | ATCCAACTCC | TTCGCTATCC | 600 |
| GCTATGGTCG | TTAATACTTT | CAAGCTCCGA | AGTAACATCA | AAAGCTTTAA | TCTAGGAGGA | 660 |
| ATGGGTTGTA | GTGCTGGTGT | TATTGCCATT | GATTTGGCTA | AAGACTTGTT | GCATGTTCAT | 720 |
| AAAAACACTT | ATGCTCTTGT | GGTGAGCACT | GAGAACATCA | CACAAGGCAT | TTATGCTGGA | 780 |
| GAAAATAGAT | CAATGATGGT | TAGCAATTGC | TTGTTTCGTG | TTGGTGGGGC | CGCGATTTTG | 840 |
| CTCTCTAACA | AGTCGGGAGA | CCGGAGACGG | TCCAAGTACA | AGCTAGTTCA | CACGGTCCGA | 900 |
| ACGCATACTG | GAGCTGATGA | CAAGTCTTTT | CGATGTGTGC | AACAAGAAGA | CGATGAGAGC | 960 |
| GGCAAAATCG | GAGTTTGTCT | GTCAAAGGAC | ATAACCAATG | TTGCGGGGAC | AACACTTACG | 1020 |
| AAAAATATAG | CAACATTGGG | TCCGTTGATT | CTTCCTTTAA | GCGAAAAGTT | TCTTTTTTTC | 1080 |
| GCTACCTTCG | TCGCCAAGAA | ACTTCTAAAG | GATAAAATCA | AGCATTACTA | TGTTCCGGAT | 1140 |
| TTCAAGCTTG | CTGTTGACCA | TTTCTGTATT | CATGCCGGAG | GCAGAGCCGT | GATCGATGAG | 1200 |
| CTAGAGAAGA | ACTTAGGACT | ATCGCCGATC | GATGTGGAGG | CATCTAGATC | AACGTTACAT | 1260 |
| AGATTTGGGA | ATACTTCATC | TAGCTCAATT | TGGTATGAAT | TAGCATACAT | AGAGGCAAAG | 1320 |
| GGAAGAATGA | AGAAAGGGAA | TAAAGCTTGG | CAGATTGCTT | TAGGATCAGG | GTTTAAGTGT | 1380 |
| AATAGTGCGG | TTTGGGTGGC | TCTACGCAAT | GTCAAGGCAT | CGGCAAATAG | TCCTTGGCAA | 1440 |
| CATTGCATCG | ATAGATATCC | GGTTAAAATT | GATTCTGATT | TGTCAAAGTC | AAAGACTCAT | 1500 |
| GTCCAAAACG | GTCGGTCCTA | ATTTGATGTA | TCTGAGTGCC | AACGTTTACT | TTGTCTTTCC | 1560 |
| TTTCTTTTAT | TGGTTATGAT | TAGATGTTTA | CTATGTTCTC | TCTTTTTCGT | TATAAATAAA | 1620 |

GAAGTTCAAT TCTTCTATAA A                                                    1641

(2) INFORMATION FOR SEQ ID NO:2:

(i) SEQUENCE CHARACTERISTICS:
       (A) LENGTH: 506 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Protein
       (B) LOCATION: 1..506
       (D) OTHER INFORMATION: /note= "Amino acid sequence of FAE1
             protein."

(xi) SEQUENCE DESCRIPTION: SEQ ID NO:2:

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
                100                 105                 110

Arg Asn Val Ala Cys Asp Asp Pro Ser Ser Leu Asp Phe Leu Arg Lys
            115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
    195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
    275                 280                 285

Arg Arg Ser Lys Tyr Lys Leu Val His Thr Val Arg Thr His Thr Gly
    290                 295                 300

Ala Asp Asp Lys Ser Phe Arg Cys Val Gln Gln Glu Asp Asp Glu Ser

|                    305              310              315              320                      |
|------|

Gly Lys Ile Gly Val Cys Leu Ser Lys Asp Ile Thr Asn Val Ala Gly
                    325                            330                       335

Thr Thr Leu Thr Lys Asn Ile Ala Thr Leu Gly Pro Leu Ile Leu Pro
                    340                            345                       350

Leu Ser Glu Lys Phe Leu Phe Phe Ala Thr Phe Val Ala Lys Lys Leu
                    355                            360                       365

Leu Lys Asp Lys Ile Lys His Tyr Tyr Val Pro Asp Phe Lys Leu Ala
                    370                            375                       380

Val Asp His Phe Cys Ile His Ala Gly Gly Arg Ala Val Ile Asp Glu
385                            390                            395                       400

Leu Glu Lys Asn Leu Gly Leu Ser Pro Ile Asp Val Glu Ala Ser Arg
                    405                            410                       415

Ser Thr Leu His Arg Phe Gly Asn Thr Ser Ser Ser Ile Trp Tyr
                    420                            425                       430

Glu Leu Ala Tyr Ile Glu Ala Lys Gly Arg Met Lys Lys Gly Asn Lys
                    435                            440                       445

Ala Trp Gln Ile Ala Leu Gly Ser Gly Phe Lys Cys Asn Ser Ala Val
                    450                            455                       460

Trp Val Ala Leu Arg Asn Val Lys Ala Ser Ala Asn Ser Pro Trp Gln
465                            470                            475                       480

His Cys Ile Asp Arg Tyr Pro Val Lys Ile Asp Ser Asp Leu Ser Lys
                    485                            490                       495

Ser Lys Thr His Val Gln Asn Gly Arg Ser
                    500                            505

(2) INFORMATION FOR SEQ ID NO:3:

(i) SEQUENCE CHARACTERISTICS:
        (A) LENGTH: 383 base pairs
        (B) TYPE: nucleic acid
        (C) STRANDEDNESS: both
        (D) TOPOLOGY: both (ii) MOLECULE TYPE: DNA (genomic)

(ix) FEATURE:
        (A) NAME/KEY: misc_feature
        (B) LOCATION: 1..383
        (D) OTHER INFORMATION: /standard_name= "partial nucleotide
            sequence of B. napus FAE1 gene"

(xi) SEQUENCE DESCRIPTION: SEQ ID NO:3:

```
TCGAACGCAT ACCGGAGCTG ACGACAAGTC TTTTCGTTGC GTGCAACAAG GAGACGATGA      60

GAACGGCAAA ATCGGAGTGA GTTTGTCCAA GGACATAACC GATGTTGCTG GTCGAACGGT     120

TAAGAAAAAC ATAGCAACGT TGGGTCCGTT GATTCTTCCG TTAAGCGAGA AACTTCTTTT     180

TTTCGTTACC TTCATGGGCA AGAAACTTTT CAAAGATAAA ATCAAACATT ACTACGTCCC     240

GGATTTCAAA CTTGCTATTG ACCATTTTTG TATACACCGG AGCAGAGCCG TGATTGATGT     300

GCTAGAGAAG AACCTAGCCC TAGCACCGAT CGATGTAGAG GCATCAAGAT CAACGTTACA     360

TAGATTTGGA AACACTTCAT CTA                                             383
```

(2) INFORMATION FOR SEQ ID NO:4:

(i) SEQUENCE CHARACTERISTICS:
        (A) LENGTH: 127 amino acids
        (B) TYPE: amino acid
        (C) STRANDEDNESS: Not Relevant
        (D) TOPOLOGY: Not Relevant

```
    (ii) MOLECULE TYPE: peptide (ix) FEATURE:
         (A) NAME/KEY: Protein
         (B) LOCATION: 1..116
         (D) OTHER INFORMATION: /note= "partial amino acid sequence
             of B. napus FAE1 protein"

(xi) SEQUENCE DESCRIPTION: SEQ ID NO:4:

Arg Thr His Thr Gly Ala Asp Asp Lys Ser Phe Arg Cys Val Gln Gln
    -10              -5                   1                   5

Gly Asp Asp Glu Asn Gly Lys Ile Gly Val Ser Leu Ser Lys Asp Ile
                 10                  15                  20

Thr Asp Val Ala Gly Arg Thr Val Lys Lys Asn Ile Ala Thr Leu Gly
             25                  30                  35

Pro Leu Ile Leu Pro Leu Ser Glu Lys Leu Leu Phe Phe Val Thr Phe
                 40                  45                  50

Met Gly Lys Lys Leu Phe Lys Asp Lys Ile Lys His Tyr Tyr Val Pro
55                   60                  65

Asp Phe Lys Leu Ala Ile Asp His Phe Cys Ile His Arg Ser Arg Ala
70                   75                  80                  85

Val Ile Asp Val Leu Glu Lys Asn Leu Ala Leu Ala Pro Ile Asp Val
                 90                  95                 100

Glu Ala Ser Arg Ser Thr Leu His Arg Phe Gly Asn Thr Ser Ser
                105                 110                 115

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (ix) FEATURE:
         (A) NAME/KEY: Region
         (B) LOCATION: 6..14
         (D) OTHER INFORMATION: /note= "Xaa means any amino acid."

(xi) SEQUENCE DESCRIPTION: SEQ ID NO:5:

Leu Ala Lys Asp Leu Xaa Xaa Xaa Xaa Xaa Xaa Xaa Xaa Xaa Leu Val
1               5                   10                  15
Val (2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (ix) FEATURE:
         (A) NAME/KEY: Region
         (B) LOCATION: 3
         (D) OTHER INFORMATION: /note= "Xaa can be either F or Y."

(ix) FEATURE:
         (A) NAME/KEY: Region
         (B) LOCATION: 4
         (D) OTHER INFORMATION: /note= "Xaa can be either G or A."
```

-continued

```
    (ix) FEATURE:
         (A) NAME/KEY: Region
         (B) LOCATION: 8..10
         (D) OTHER INFORMATION: /note= "Xaa means any amino acid."

(xi) SEQUENCE DESCRIPTION: SEQ ID NO:6:

Gly Cys Xaa Xaa Gly Gly Thr Xaa Xaa Xaa
1               5                   10

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /standard_name= "Primer FL125"

(xi) SEQUENCE DESCRIPTION: SEQ ID NO:7:

CGGTTATACG ATAACGGTCG                                              20

(2) INFORMATION FOR SEQ ID NO:8:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /standard_name= "Primer JK30"

(xi) SEQUENCE DESCRIPTION: SEQ ID NO:8:

GTACGATGAA GTGGTTAGCC                                              20
```